United States Patent [19]
Larson et al.

[11] Patent Number: 5,243,410
[45] Date of Patent: Sep. 7, 1993

[54] OPTICAL MIXER

[75] Inventors: Donald E. Larson, Geneseo; Carl F. Leidig, Rochester; Raymond S. Burbott, Spencerport; John A. Quenin; Daniel P. Salotto, both of Rochester, all of N.Y.

[73] Assignee: Eastman Kodak Company, Rochester, N.Y.

[21] Appl. No.: 789,718

[22] Filed: Nov. 8, 1991

[51] Int. Cl.⁵ .............................................. G01N 21/55
[52] U.S. Cl. .................................... 356/445; 356/446; 356/236; 250/228; 362/32; 362/335; 359/599
[58] Field of Search ............. 356/445, 446, 236; 250/228; 362/32, 335; 359/599, 868, 869

[56] References Cited

U.S. PATENT DOCUMENTS

| | | | |
|---|---|---|---|
| 2,981,826 | 4/1961 | Mattern | 362/32 |
| 3,300,646 | 1/1967 | Casebeer | 250/228 |
| 4,660,984 | 4/1987 | MacDonald | 356/446 |
| 4,747,030 | 5/1988 | Offner et al. | 362/302 |
| 4,988,205 | 1/1991 | Snail | 356/446 |
| 5,051,872 | 9/1991 | Anderson | 362/32 |

OTHER PUBLICATIONS

"High Collection Nonimaging Optics", Welford et al, p. 4 Academic Press, 1989.

Primary Examiner—Vincent P. McGraw
Assistant Examiner—LaCharles Keesee
Attorney, Agent, or Firm—Dressler, Goldsmith, Shore, Sutker & Milnamow, Ltd.

[57] ABSTRACT

A high efficiency optical mixer includes a source of focused radiant energy. The focused radiant energy is concentrated by a parabolic concentrator onto an exit port. A diffuse reflector, which can be planar or arcuate, is maintained in contact with the output port thereby minimizing optical losses and diffusely reflecting light from the concentrator. The reflected light can be transmitted, by fiber optics, to an optical system. A method is providing for concentrating focused radiant energy onto a selected area and diffusely reflecting same from that area.

29 Claims, 3 Drawing Sheets

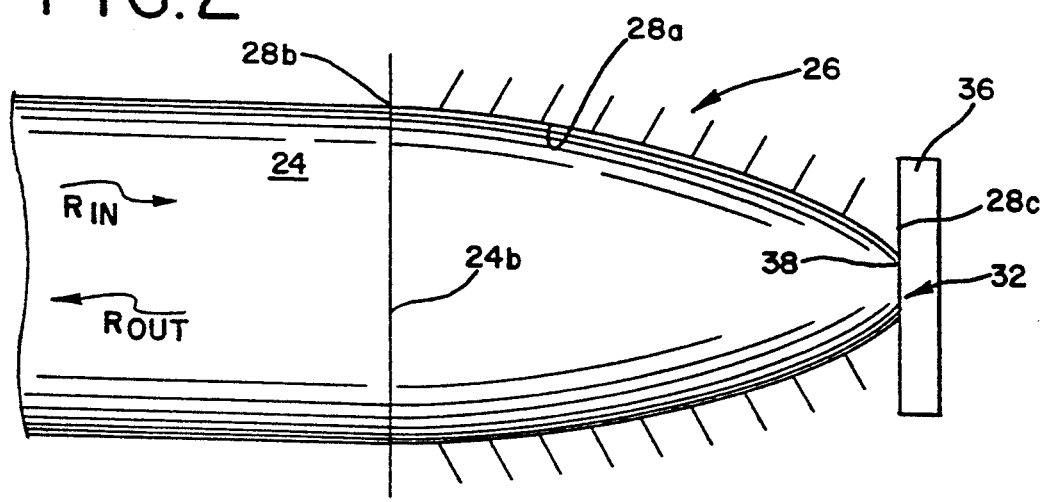
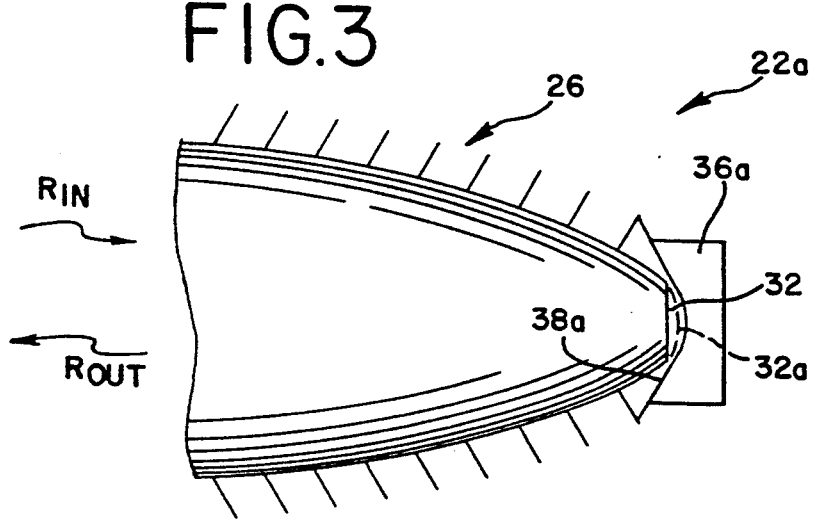
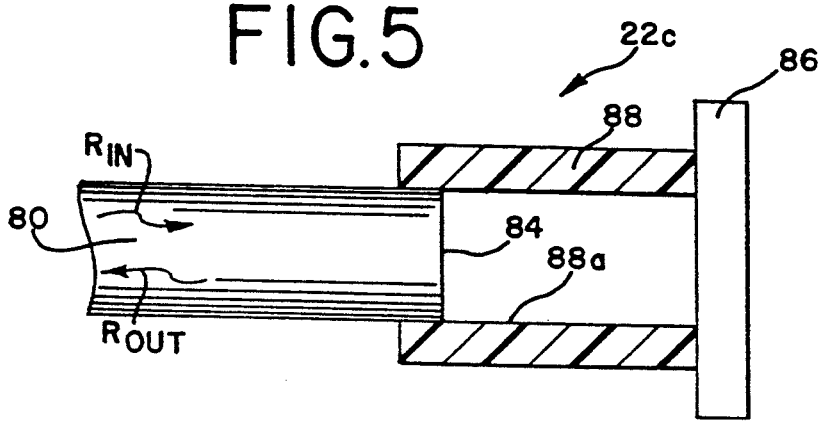

OPTICAL MIXER

FIELD OF THE INVENTION

The invention pertains to an apparatus and method for generating a uniform radiant energy source. More particularly, the invention pertains to an improved mixer and method of optical mixing to produce a uniform light source.

BACKGROUND OF THE INVENTION

Pulsed sources of radiant energy, such as xenon sources, have been used in various types of optical systems. However, the structure and the position of the light source can vary from pulse to pulse thereby resulting in a structured as opposed to a diffused, more uniform, radiant energy signal.

The problem has been recognized and one solution has been previously disclosed in MacDonald U.S. Pat. No. 4,660,984 entitled "Reflectometer Featuring An Integrated Cavity of Enhanced Efficiency", assigned to the Assignee of the present invention. The reflectometer of the MacDonald patent provides mixing of a pulsed radiant energy signal for the purpose of generating a more uniform output signal.

While the structure of the MacDonald patent does provide a uniform radiant energy signal, the disclosed apparatus for achieving that result is relatively expensive. There continues to be a need for radiant energy mixing structures which provide a uniform output radiant energy signal, with minimum losses, using inexpensive components. It would further be desirable if such mixing structures are physically small and light weight so as to be readily usable with a variety of optical systems.

SUMMARY OF THE INVENTION

A high efficiency, low loss, optical mixer directs a focused source of radiant energy onto an output area of a concentrator. A diffuse reflector, which can be planar or arcuate, is maintained in contact with the concentrator at the output area.

Concentrated radiant energy incident on the output area is diffusely reflected, by the reflector, back out of the concentrator. Because the concentrator and the diffuse reflector are in physical contact within one another, there are no gaps through which diffusely reflected radiant energy can be lost.

The concentrator can be formed with a generally parabolic mirrored surface of revolution. The focused source of radiant energy can be energized continuously or intermittently.

Because the diffused reflector is in physical contact with the output port of the concentrator, the diffuse reflections all take place at that region. The diffusely reflected radiant energy can be conducted, via a fiber optic bundle, to an optical system for distribution.

A method of providing a uniform radiant energy signal at an output port includes generating a focused beam of radiant energy. The beam is then concentrated in a selected area. The concentrated beam is diffusely reflected only at the selected area and then directed to the output port.

The beam of radiant energy can be intermittently generated or continuously generated. The concentrating step can include reflecting the beam at least in part parabolically onto the predetermined area.

The diffuse reflecting step can be carried out using either a planar diffuse reflector or an arcuate diffuse reflector. In both instances, the diffuse reflector is coextensive with the area onto which the beam has been concentrated.

Numerous other advantages and features of the present invention will become readily apparent from the following detailed description of the invention and the embodiments thereof, from the claims and from the accompanying drawings in which the details of the invention are fully disclosed as a part of this specification.

BRIEF DESCRIPTION OF THE DRAWING

FIG. 2 is an enlarged, fragmentary view of a portion of the apparatus of FIG. 1;

FIG. 3 is an enlarged, fragmentary view of a portion of the apparatus of FIG. 1 illustrating an alternate mixer structure;

FIG. 5 is an enlarged, fragmentary view, partly in section illustrating yet another mixer structure in accordance with the present invention.

DETAILED DESCRIPTION OF THE PREFERRED EMBODIMENTS

Figure 1:
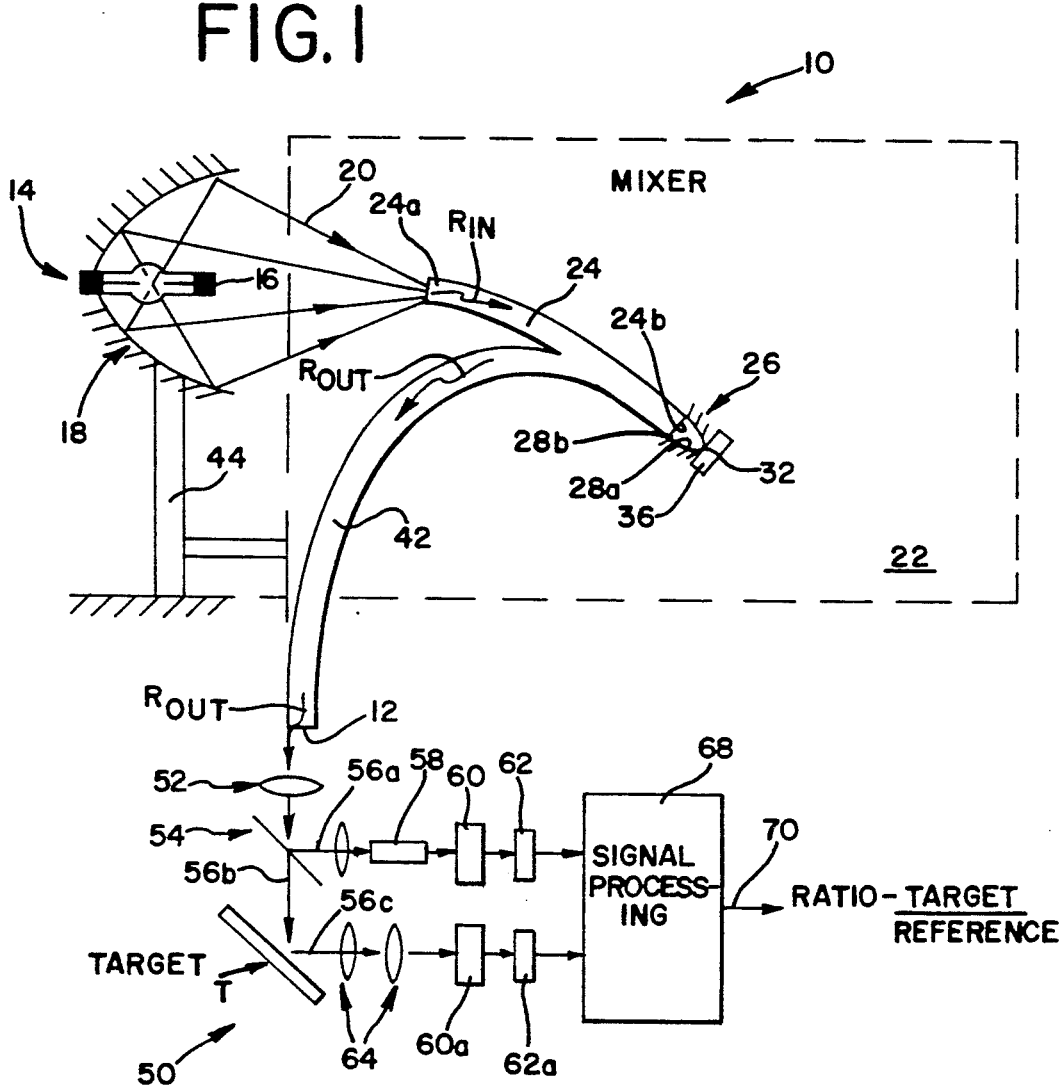
FIG. 1 is an overall schematic view of an optical mixing apparatus and method in accordance with the present invention.

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

With respect to FIG. 1, a system 10 is illustrated which provides uniform radiant energy $R_{OUT}$ at an output port 12 from an imperfect, non-uniform ultraviolet or visible radiant energy source 14.

The source 14 includes an intermittently energizeable source of radiant energy 16. The source 16 can be, for example, a Xenon arc light or alternate form of arc source.

A collection reflector 18 in part surrounds the source 16 for focusing a radiant energy output beam 20 therefrom. The beam 20 is directed into a mixer 22 and is a source of radiant energy $R_{IN}$ input to the mixer 22.

The mixer 22 includes a first fiber optic member 24 for transmitting incident non-uniform radiant energy $R_{IN}$ from the beam 20 in a first direction toward a concentrator 26. The member 24 has a first, energy receiving, end 24a and a second, planar energy output, end 24b.

The concentrator 26 includes a mirrored surface of revolution 28a (best seen in FIG. 2) which forms an essentially parabolic cone mirror. The concentrator 26 has an input port 28b for receipt of the radiant energy $R_{IN}$ and an output port 28c. The theory and operation of such concentrators are discussed in a book, *High Collection Non-imaging Optics*, by Welford and Winston, published by Academic Press, Inc., 1989.

The input port 28b of the concentrator 26 is positioned adjacent to the planar end 24b of the fiber optic member 24. A light tight seal is provided between planar end 24b and the input port 28b.

The concentrator 26 focuses the non-uniform radiant energy $R_{IN}$ transmitted by the fiber optic member 24 onto a relatively small, circular area 32 at the output port 28c.

A diffuse reflector 36 is positioned adjacent to and in contact with the area of optical concentration 32 at the output port 28c. The diffuse reflector 36 has a planar surface 38 which is in contact with the output port 28c. This physical contact minimizes losses while receiving radiant energy $R_{IN}$ and reflecting back radiant energy $R_{OUT}$ in a direction opposite the first direction.

A second fiber optic transmission element 42 can be used to transmit the diffuse radiant energy $R_{OUT}$ to the output port 12. The fiber optic members 24 and 42 can be formed as part of a bifurcated fiber bundle.

The source 16 is preferably located at one focus of an ellipsoidal reflector. The planar output surface 24b is then located at a second focus thereof.

FIG. 3 illustrates a portion of an alternate mixer structure 22a. In the structure 22a, the planar output port 32 of the concentrator is juxtaposed to and in contact with a diffuse reflector 36a with a non-planar, arcuate reflecting surface 38a. The arcuate surface 38a can be either concave or convex provided its surface has an overall diameter which exceeds the diameter of the exit port 32 so as to completely cover the exit port. The exit port 32 can alternately be formed with an arcuate surface 32a provided the previous condition is met.

The system 10 can be supported by a bracket or base structure 44. The details of the structure 44 are not a limitation of the present invention.

Again with reference to FIG. 1, diffuse radiant energy $R_{OUT}$ which exits the output port 12 can be directed toward an optical system 50. The purpose of the optical system 50 is to split the uniform radiant energy output $R_{OUT}$ into a reference beam and a target beam for analysis of a target T.

Radiant energy $R_{OUT}$ from the port 12 is first passed through a projection lens 52 and then onto a beam splitter 54. A reference beam 56a is directed, via a fiber optic transmission member 58, through a color discriminator 60 and onto a reference photodetector 62.

A target beam 56b which exits the beam splitter 54 is directed onto target T being evaluated. A reflected target beam 56c is directed, via focusing and pick-up lens system 64, through a color discriminator 60a and onto a target photodetector 62a.

Outputs from the photodetectors 62 and 62a are processed in circuitry 68 to form a ratio on a line 70 of the reflected target beam to the reference beam.

It will be understood that the optical system 50 is illustrated for example purposes only and is not a limitation of the present invention. The present invention is usable with a wide variety of optical systems.

Figure 4:
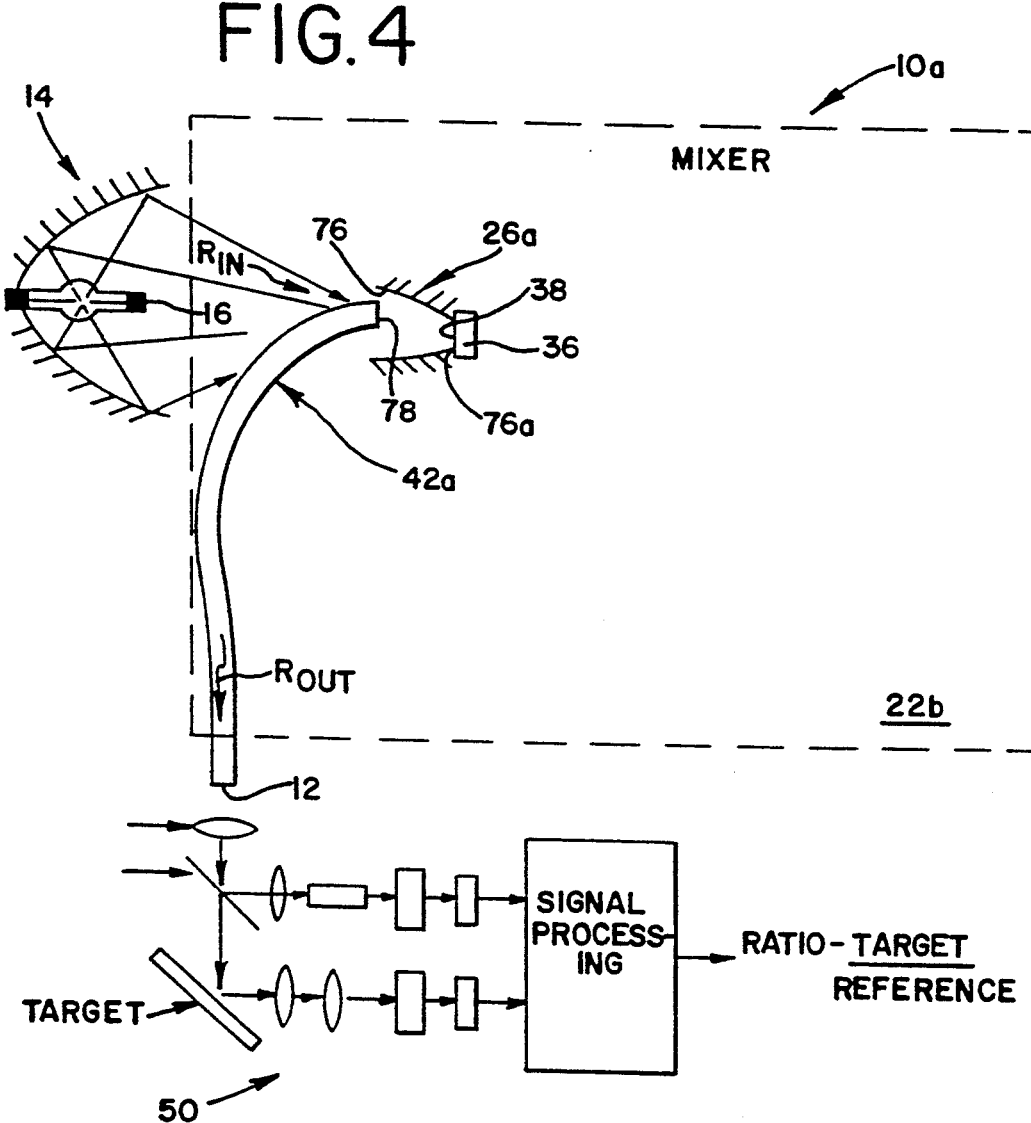
FIG. 4 is an overall schematic view of an alternate mixing apparatus in accordance with the present invention.

FIG. 4 illustrates an alternate system 10a for generating a uniform radiant energy beam at the output port 12. The system 10a utilizes a triggerable arc source such as the source 14 previously discussed.

Focused radiant energy $R_{IN}$ from the source 14 is transmitted in a first direction toward a concentrator 26a. The lamp 16 can be located at one focus of an ellipsoidal reflector. The concentrator 26a is located at the second focus of that reflector.

The concentrator 26a includes a mirrored surface of revolution with a substantially parabolic shape. The concentrator 26a includes an input port 76 and an output port 76a.

A diffuse reflector, such as the diffuse reflector 36, is physically in contact with and covers the output port 78a of the concentrator 26a. The illustrated reflector 36 has a planar diffuse reflecting surface 38 although it too could be an arcuate surface as is surface 38a.

Incident radiant energy $R_{IN}$ which enters the concentrator 26a at the first end 76 thereof is concentrated at the exit port 76a. The concentrated radiant energy is then reflected by the diffuse reflector 36 back toward the input port 76.

A portion of the reflected diffuse radiant energy is picked up at a planar input end 78 of a fiber optic member 42a and transmitted to the output port 12. Once the radiant energy $R_{OUT}$ exits from the output port 12, it can be utilized in an optical system such as the previously discussed system 50.

FIG. 5 illustrates a portion of an alternate mixer structure 22c. The mixer 22c includes a bifurcated fiber optic member 80 with a radiant energy planar input surface, not illustrated, which receives incident radiant energy $R_{IN}$. The member 80 includes a planar, radiant energy input/output surface 84 and a uniform, diffuse radiation output port, such as the output port 12 from which diffuse radiant energy $R_{OUT}$ exits.

The planar radiant energy input/output surface 84 is optically coupled to a diffuse reflector 86. A hollow housing 88 between the input/output end 84 and the diffuse reflector 86 minimizes losses of input radiant energy $R_{IN}$ and diffuse radiant energy output $R_{OUT}$. The housing 88 can include an interior reflecting surface 88a.

The mixer 22c can be used in conjunction with a triggerable source of radiant energy such as the source of illumination 14. The mixer 22c is advantageous in that it is inexpensive, small and light weight.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

We claim:

1. An optical mixer for providing uniform radiant energy at a selected site comprising:
   a source of focused radiant energy;
   a parabolic member including a tapered reflecting surface for receiving the focused energy from said source and concentrating same onto a predetermined output port having a selected area;
   a diffuse reflector in contact with said output port for reflecting concentrated energy incident thereon; and
   means for transmitting at least a portion of the reflected energy to the selected site.

2. An optical mixer as in claim 1 including means for energizing said source of energy.

3. An optical mixer as in claim 1 wherein said source includes a reflector.

4. An optical mixer as in claim 1 wherein said diffuse reflector has a planar surface in contact with said output port.

5. An optical mixer for providing uniform radiant energy at a selected site comprising:
   a source of focused radiant energy;

a parabolic member for receiving the focused energy from said source and concentrating same onto a predetermined output port having a selected area;

a diffuse reflector in contact with said output port for reflecting concentrated energy incident thereon; and means for transmitting at least a portion of the reflected energy to the selected site;

wherein said output port has a generally circular perimeter with a first radius and said diffuse reflector has a curved surface with a radius of curvature greater than said first radius.

6. An optical mixer as in claim 5 wherein said perimeter of said output port is in contact with said curved surface of said reflector thereby minimizing loss of reflected radiant energy.

7. An optical mixer as in claim 1 including means for transmitting said focused radiant energy to said parabolic member.

8. An optical mixer as in claim 1 wherein said parabolic member has a reflective parabolic surface of revolution.

9. An optical mixer comprising:
a support member;
means, carried on said support member, for generating radiant energy;
means, including a parabolic member having a tapered reflecting surface and an exit port, displaced from said generating means and carried on said support member, for concentrating said radiant energy at said exit port; and
means, covering said exit port, for diffusely reflecting said concentrated radiant energy.

10. An optical mixer as in claim 9 including means for conducting said reflected radiant energy from said reflecting means.

11. An optical mixer as in claim 10 wherein said conducting means includes a fiber optic element.

12. An optical mixer as in claim 9 including means for focusing said generated radiant energy.

13. An optical mixer as in claim 9 wherein said reflecting means includes a substantially planar reflecting surface.

14. An apparatus for mixing a focused beam of radiant energy and directing the mixed beam to an output port comprising:
a first reflector having an input region oriented to receive the focused beam and a planar output region whereat the reflected beam is concentrated;
a second reflector in contact with at least part of said first reflector at said output region for diffusely reflecting the concentrated beam; and
means, optically coupled to said second reflector, for transmitting the diffusely reflected beam to the output port;
wherein said transmitting means includes a bifurcated fiber optic element.

15. An apparatus as in claim 14 wherein said second reflector is a planar diffuse reflector.

16. An apparatus as in claim 14 including a fiber optic transmission member for directing the focused beam of radiant energy onto the first reflector.

17. An apparatus as in claim 14 wherein said first reflector is a substantially parabolic reflector.

18. An apparatus as in claim 17 wherein said output region has a circular periphery.

19. An apparatus as in claim 17 wherein said first reflector includes a fiber optic member with first and second ends, said first end oriented to receive focused radiant energy with said second end oriented to direct radiant energy out of said substantially parabolic reflector.

20. An optical mixer for providing a source of uniform radiant energy comprising:
a parabolic reflector with a circular cross section, a first end and a second end, said second end having a smaller cross section than said first end;
a diffuse reflector in contact with said second end;
an optical conduit with first and second ends, said first end optically coupled to said diffuse reflector with said second end an output port for the substantially uniform radiant energy; and
a second optical conduit with third and fourth ends, said third end optically couplable to the source, said fourth end optically coupled to said parabolic reflector.

21. A mixer as in claim 20 wherein said diffuse reflector has an arcuate reflecting surface.

22. A method of providing a uniform radiant energy signal at an output port comprising:
generating a focused beam of radiant energy;
concentrating the beam in a selected substantially circular area by directing the beam through a parabolic concentrator with a tapered reflecting surface which substantially reflects the beam to a concentrated energy output port positioned at the selected area;
diffusely reflecting the concentrated beam only at the selected area; and
directing the reflected, diffuse radiant energy to the output port.

23. A method as in claim 22 including intermittently generating the beam of radiant energy.

24. A method as in claim 22 including confining the focused beam of radiant energy to a predetermined transmission path extending between a location where the beam is generated and the selected area.

25. A method as in claim 22 including providing a substantially planar diffuse reflector at the selected area.

26. A mixer usable with a source of radiant energy for producing a uniform radiant energy output comprising:
a substantially parabolic member having a tapered reflecting surface, said parabolic member having first and second ends for directing incident radiant energy that passes through said first end toward said second end to a first surface defined, at said second end; and
a diffuse reflector in contact with and covering said second end for diffusely reflecting concentrated radiant energy back toward said first end.

27. A mixer as in claim 26 including a radiant energy conductor with an input port optically coupled to said diffuse reflector for receiving at least part of the diffusely reflected radiant energy and with an output port for providing the radiant energy output.

28. A method of generating uniform radiant energy from a source of focused non-uniform radiant energy comprising:
transmitting the non-uniform radiant energy in a first direction;
reflecting the transmitted radiant energy and concentrating said onto a predetermined circular surface; and
diffusely reflecting the concentrated radiant energy only from the surface and substantially opposite to the first direction.

29. A method of generating uniform radiant energy as in claim 28 including transmitting the oppositely reflected, diffuse radiant energy to a selected output port.

* * * * *